United States Patent [19]
Meinke et al.

[11] Patent Number: 5,922,837
[45] Date of Patent: Jul. 13, 1999

[54] ANTIPROTOZOAL CYCLIC TETRAPEPTIDES

[75] Inventors: Peter T. Meinke, New York, N.Y.; Sandra J. Rattray, Somerset; Dennis M. Schmatz, Cranford, both of N.J.

[73] Assignee: Merck & Co., Inc., Rahway, N.J.

[21] Appl. No.: 08/789,347

[22] Filed: Jan. 27, 1997

Related U.S. Application Data

[60] Provisional application No. 60/010,931, Jan. 31, 1996.

[51] Int. Cl.$^6$ ...................................................... C07K 5/00
[52] U.S. Cl. ........................................... 530/317; 530/318
[58] Field of Search ..................... 514/9, 11; 530/317, 530/318

[56] References Cited

U.S. PATENT DOCUMENTS

| | | | |
|---|---|---|---|
| 4,218,478 | 8/1980 | Omura et al. | 424/324 |
| 5,356,927 | 10/1994 | Taraschi et al. | 514/449 |
| 5,620,953 | 4/1997 | Cannova et al. | 514/18 |

FOREIGN PATENT DOCUMENTS

| | | |
|---|---|---|
| 406725 | 9/1991 | European Pat. Off. . |
| WO 96/03428 | 2/1996 | WIPO . |

OTHER PUBLICATIONS

CA 123:337548, 1995.
Bioassays, 17(5): p. 423, 1995.
J. Biol. Chem. 268(30): p. 22429, 1993.
J. Antibiot., 43(12): p. 1524, 1990.
Acta Cryst. C, 47: p. 1469, 1991.
Jap. J. Cancer Res., 83(4): p. 324, 1992.
J. Med. Chem., 30: p. 71, 1987.
Experientia, 41: p. 348, 1985.
Biochimie, 71: p. 71, 1989.
Tet. Lett., 35(33): p. 6009, 1994.
Biochem., 22: p. 3507, 1983.
J. Med. Chem., 24: p. 567, 1981.
Amino Acids, 6(3): p. 315, 1994.
Biochem., 22: p. 3502, 1983.
Eur. J. Cancer, 10:801, 1974.
Phytopathology, 57: p. 1169, 1967.
Biochem. Biophys. Res. Comm. 107:785, 1982.
Bioch J., 1994, 303: 723–729.
J. Biol. Chem., 1990, 265:17174.

*Primary Examiner*—Sheela Huff
*Attorney, Agent, or Firm*—Mollie M. Yang; David L. Rose

[57] ABSTRACT

The present invention provides novel cyclic tetrapeptides useful in the treatment or prevention of protozoal diseases; in particular, the novel compounds are active against the causative pathogens in malaria, toxoplasmosis, and coccidiosis. The invention also relates to the use of known compounds which are histone deacetylase inhibitors as antiprotozoal agents.

2 Claims, No Drawings

ANTIPROTOZOAL CYCLIC TETRAPEPTIDES

CROSS REFERENCE TO RELATED APPLICATIONS

This application is based on, and claims priority from, provisional application no. 60/010,931 filed Jan. 31, 1996.

BACKGROUND OF THE INVENTION

Parasitic protozoa are responsible for a wide variety of infections in man and animals. Many of the diseases are life threatening to the host and cause considerable economic loss in animal husbandry. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii, Toxoplasma gondii*, Cryptosporidium sp. are becoming increasingly significant in the developed countries.

A protozoal infection of great economic importance is coccidiosis, a widespread disease of domesticated animals produced by infections by protozoa of the genus Eimeria. Some of the most significant of Eimeria species are those in poultry namely *E. tenella, E. acervulina, E. necatrix, E. brunetti* and *E. maxima*. The disease is responsible for high levels of morbidity and mortality in poultry and can result in extreme economic losses.

In some protozoal diseases, such as Chagas disease, there is no satisfactory treatment; in others, drug-resistant strains of the protozoa may develop. Accordingly, there exists a continued need to identify new and effective anti-protozoal drugs. However, antiparasitic drug discovery has been, for the most part, a random and laborious process through biological screening of natural products and synthetic compounds against a panel of parasites. This process can be greatly facilitated and made more specific if a target of antiprotozoal drugs can be identified, and incorporated into the screening process.

Histone deacetylase and histone acetyltransferase together control the net level of acetylation of histones. Inhibition of the action of histone deacetylase results in the accumulation of hyperacetylated histones, which in turn is implicated in a variety of cellular responses, including altered gene expression, cell differentiation and cell-cycle arrest. Recently, trichostatin A and trapoxin A have been reported as reversible and irreversible inhibitors, respectively, of mammalian histone deacetylase (see e.g., Yoshida et al., BioEssays, 1995, 17(5):423–430). Trichostatin A has also been reported to inhibit partially purified yeast histone deacetylase (Sanchez del Pino et al., Biochem. J., 1994, 303:723–729). Trichostatin A is an antifungal antibiotic and has been shown to have anti-trichomonal activity as well as cell differentiating activity in murine erythroleukemia cells, and the ability to induce phenotypic reversion in sis-transformed fibroblast cells (see e.g. U.S. Pat. No. 4,218,478; Yoshida et al., BioEssays, 1995, 17(5):423–430 and references cited therein). Trapoxin A, a cyclic tetrapeptide, induces morphological reversion of v-sis-transformed NIH3T3 cells (Yoshida and Sugita, Jap. J. Cancer Res., 1992, 83(4):324–328). The present inventors have found that a number of cyclic tetrapeptides structurally related to trapoxin A are inhibitors of histone deacetylase and also possess antiprotozoal activity.

SUMMARY OF THE INVENTION

The present invention relates to novel cyclic tetrapeptides and pharmaceutical compositions containing said tetrapeptides. The invention also concerns a method for treating protozoal infections by administering to a host suffering from protozoal infection a therapeutically effective amount of a compound that inhibits histone deacetylase. Additionally, the invention relates to the use of known cyclic tetrapeptides as inhibitors of histone deacetylase which are useful as antiprotozoal agents.

DETAILED DESCRIPTION OF THE INVENTION

In one aspect, the present invention relates to novel cyclic tetrapeptides having the formula I:

SEQUENCE ID NO.: 1 wherein
A is

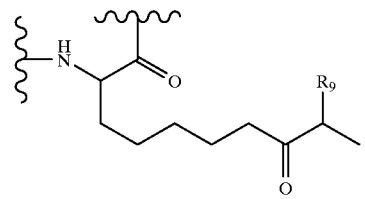

$R_9$ is H, OH, $OPO_3=$, $OC(O)R^a$, $OCO_2R^a$ or $OC(O)NR^aR^a$;

wherein
$R^a$ is
(1) optionally substituted $C_1$–$C_{10}$ alkyl,
(2) optionally substituted $C_3$–$C_{10}$ alkenyl,
(3) optionally substituted $C_3$–$C_{10}$ alkynyl,
(4) optionally substituted aryl,
(5) optionally substituted $C_3$–$C_8$ cycloalkyl
(6) optionally substituted $C_5$–$C_8$ cycloalkenyl where the substitutents on the alkyl, alkenyl, alkynyl, aryl, cycloalkyl and cycloalkenyl are from 1 to 5 groups independently selected from hydroxy, $C_1$–$C_6$ alkoxy, $C_3$–$C_7$ cycloalkyl, aryl $C_1$–$C_3$ alkoxy and halogen,
(7) $C_1$–$C_5$ perfluoroalkyl,
(8) a 5- or 6-membered ring containing 1 to 4 heteroatoms selected from oxygen, sulfur and nitrogen optionally substituted by 1 to 4 groups independently selected from $C_1$–$C_5$ alkyl, $C_1$–$C_5$ alkenyl, $C_1$–$C_5$ perfluoroalkyl, amino or halogen, and which may be saturated or partly unsaturated;

B is selected from the group consisting of Alanine, Arginine, Asparagine, Aspartic Acid, Cysteine, Glutamine, Glutamic Acid, Glycine, Histidine, Isoleucine, Leucine, Lysine, Methionine, Ornithine, Phenylalanine, Proline, Serine, Threonine, Tryptophan, Tyrosine, Tyrosine(OMe), Valine, α-Aminobutyric Acid, β-Cyclohexyl-Alanine, Hydroxyproline, Pipecolic Acid, Norleucine, Norvaline and β-(2-Thienyl)-Alanine;

C is selected from the group consisting of Alanine, Arginine, Asparagine, Aspartic Acid, Cysteine, Glutamine, Glutamic Acid, Glycine, Histidine, Isoleucine, Leucine, Lysine, Methionine, Ornithine, Phenylalanine, Proline, Serine, Threonine, Tryptophan, Tyrosine, Tyrosine(OMe), Valine, α-Aminobutyric Acid, β-Cyclohexyl-Alanine, Hydroxyproline, Pipecolic Acid, Norleucine, Norvaline and β-(2-Thienyl)-Alanine;

D is selected from the group consisting of Proline, Pipecolic Acid, Glycine, Alanine, Hydroxyproline, α-Aminobutyric Acid, N-Methyl-Alanine and N-Methyl-Glycine; or a pharmaceutically acceptable salt thereof.

In a second aspect, the present invention provides a method for the treatment or prevention of protozoal infections comprising administering to a host suffering from a protozoal infection a therapeutically effective amount of a compound of formula (I). A therapeutically effective amount may be one that is sufficient to inhibit histone deacetylase of the causative protozoa.

In a third aspect, the present invention provides a composition useful for the treatment or prevention of protozoal diseases which comprises an inert carrier and an effective amount of a compound of formula I.

Compounds of the present invention contain several asymmetric centers and may thus give rise to diastereomers and optical isomers. The present invention is meant to comprehend such possible diastereomers as well as their racemic and resolved, enantiomerically pure forms and pharmaceutically acceptable salts thereof.

The term "pharmaceutically acceptable salts" refers to salts prepared from pharmaceutically acceptable non-toxic bases or acids. When the compound of the present invention is acidic, salts may be prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

Preferred compounds of the present invention are those of formula I wherein the substituents are as follows:

[cyclo-(Pip-Ile-Trp-Aoh)] (SEQUENCE ID NO.: 2)
[cyclo-(Pip-Ile-Trp-Aod)] (SEQUENCE ID NO.: 3)
[cyclo-(Pro-Ile-Trp-Aoh)] (SEQUENCE ID NO.: 4)
[cyclo-(Pro-Ile-Trp-Aod)] (SEQUENCE ID NO.: 5)
[cyclo-(Pro-Ala-Ala-Aoh)] (SEQUENCE ID NO.: 6)
[cyclo-(Pro-Ala-Ala-Aod)] (SEQUENCE ID NO.: 7)
[cyclo-(Pip-Ala-Ala-Aoh)] (SEQUENCE ID NO.: 8)
[cyclo-(Pip-Ala-Ala-Aod)] (SEQUENCE ID NO.: 9)
[cyclo-(Pro-Phe-Aib-Aoh)] (SEQUENCE ID NO.: 10)
[cyclo-(Pro-Phe-Aib-Aod)] (SEQUENCE ID NO.: 11)
[cyclo-(Pip-Phe-Aib-Aoh)] (SEQUENCE ID NO.: 12)
[cyclo-(Pip-Phe-Aib-Aod)] (SEQUENCE ID NO.: 13)
[cyclo-(Pip-Leu-Phe-Aoh)] (SEQUENCE ID NO.: 14)
[cyclo-(Pip-Leu-Phe-Aod)] (SEQUENCE ID NO.: 15)
[cyclo-(Pro-Leu-Phe-Aoh)] (SEQUENCE ID NO.: 16)
[cyclo-(Pro-Leu-Phe-Aod)] (SEQUENCE ID NO.: 17)
[cyclo-(Pro-Phe-Phe-Aoh)] (SEQUENCE ID NO.: 18)
[cyclo-(Pro-Phe-Phe-Aod)] (SEQUENCE ID NO.: 19)
[cyclo-(Pip-Leu-Phe-Aoh)] (SEQUENCE ID NO.: 20)
[cyclo-(Pip-Leu-Phe-Aod)] (SEQUENCE ID NO.: 21)
[cyclo-(Pip-Ile-Tyr(OMe)-Aoh)] (SEQUENCE ID NO.: 22)
[cyclo-(Pip-Ile-Tyr(OMe)-Aod)] (SEQUENCE ID NO.: 23)
[cyclo-(Pro-Ile-Tyr(OMe)-Aoh)] (SEQUENCE ID NO.: 24)
[cyclo-(Pro-Ile-Tyr(OMe)-Aod)] (SEQUENCE ID NO.: 25)
[cyclo-(Pip-Ile-Tyr-Aoh)] (SEQUENCE ID NO.: 26)
[cyclo-(Pip-Ile-Tyr-Aod)] (SEQUENCE ID NO.: 27)
[cyclo-(Pro-Ile-Tyr-Aoh)] (SEQUENCE ID NO.: 28)
[cyclo-(Pro-Ile-Tyr-Aod)] (SEQUENCE ID NO.: 29)

where Aoh is 2-Amino-8-Oxo-9-Hydroxy-decanoic acid and Aod is 2-Amino-8-Oxo-Decanoic acid.

The concept of the inhibition of histone deacetylase as a target for antiprotozoal compounds is described in provisional application Ser. No. 60/004,065 filed Sep. 20, 1995.

Examples of known compounds which may be histone deacetylase inhibitors and therefore useful in the treatment of protozoal diseases include, but are not limited to, trichostatin A, trapoxin A, HC-toxin, chlamydocin, Cly-2, WF-3161, Tan-1746, apicidin and analogs thereof. Trichostatin A, trapoxin A, HC-toxin, chlamydocin, Cy-2, and WF-3161, as well as derivatives thereof are well known in the art. HC-Toxin is described in Liesch et al. (1982) Tetrahedron 38, 45–48; Trapoxin A is described in Itazaki et al. (1990) J. Antibiot. 43, 1524–1532; WF-3161 is described in Umehana et al. (1983) J. Antibiot. 36, 478–483; Cly-2 is described in Hirota et al (1973) Agri. Biol. Chem 37, 955–56; Chlamydocin is described in Closse et al. (1974) Helv. Chim. Acta 57, 533–545 and Tan 1746 is described in Japanese Patent No. 7196686 to Takeda Yakuhin Kogyo KK.

Apicidin and analogs thereof referred to herein have the following structural formulae:

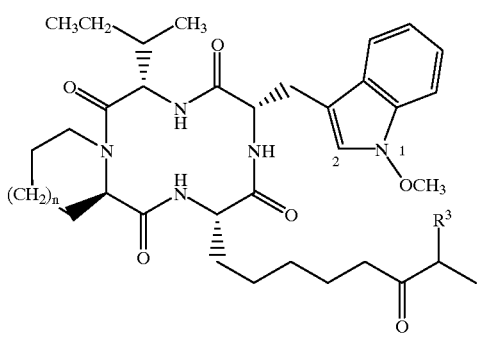

| Compound | n | R³ |
|---|---|---|
| Apicidin Ia | 1 | H |
| Ib | 0 | H |
| Ic | 1 | OH |

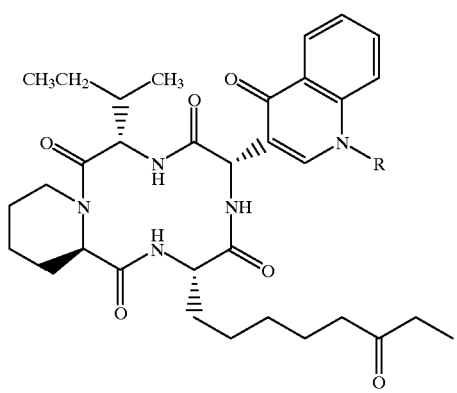

Apicidin IIa  R = OCH3
Apicidin IIb  R = H

These compounds are described in pending applications U.S. Ser. No. 08/281,325 filed Jul. 27, 1994 and 08/447,664 filed May 23, 1995 and 08/716,978 filed Sep. 20, 1996. They are produced from a strain of Fusarium as disclosed in the abovementioned applications.

Some of the known cyclic tetrapeptides which include histone deacetylase inhibitors, are shown below:

TAN-1746

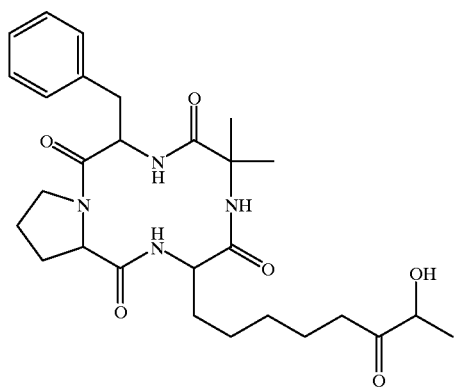

HC-Toxin

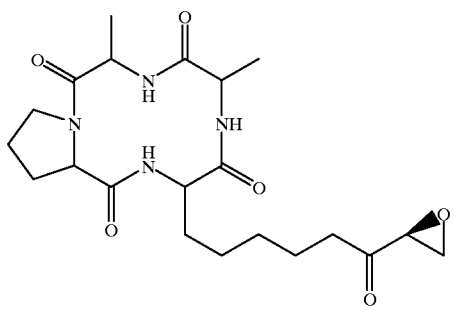

(Chlamydocin)

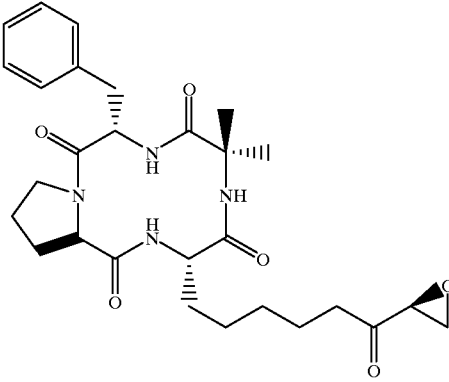

(WF-3161)

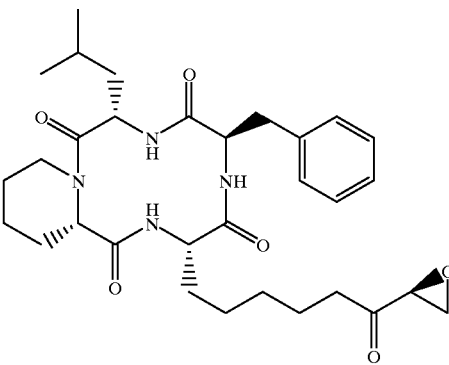

-continued (Trapoxin A)

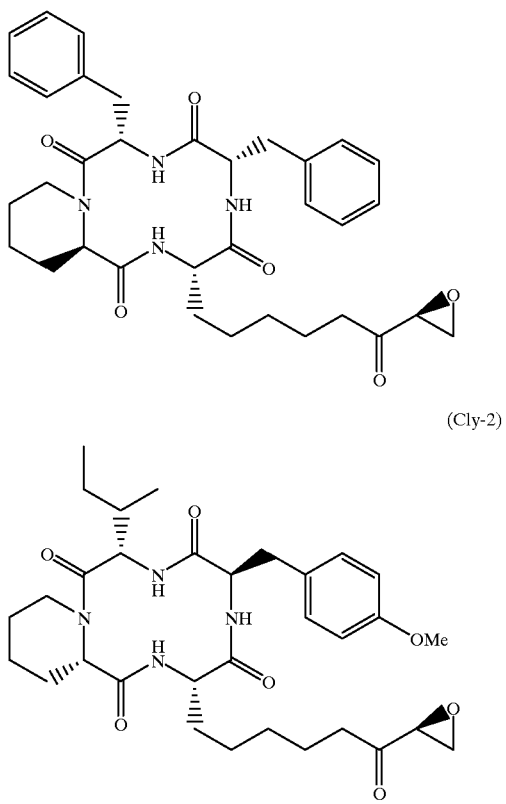

(Cly-2)

The novel compounds of formula I may be readily synthesized in solution phase or on solid phase using techniques known to those skilled in the art. Linear tetrapeptides may be synthesized either in solution phase or on solid phase resins using conditions known to those skilled in the art such as those set forth in *The Practice of Peptide Synthesis*, Bodanszky and Bodanzsky, Springer-Verlag, New York, N.Y., 1984 or *The Peptides: Analysis Synthesis, Biology*, Volume 9, Undenfriend, S. and Meienhofer J., Eds., Academic Press, Inc., San Diego, Calif., 1987 or Ho, G. J. et. al., *J. Org. Chem.*, 1995, 60, 3569 or Ehrlich, A. et al., *Tetrahedron Letters*, 1993, 30, 4781 and references cited therein).

Cyclization of the resultant linear tetrapeptides may be achieved either in solution phase or on solid phase resins using conditions known to those skilled in the art, such as those set forth in Jackson, S. et al., *J. Am. Chem. Soc.*, 1994, 116, 3220 or Zhang, L.-H. and Ma, P., *Tetrahedron Letters*, 1994, 35, 5765 or Taylor, J. W. et al., *Tetrahedron Letters*, 1990, 31, 6121 or Rihter, L. S. et al., *Tetrahedron Letters*, 1994, 31, 5547 or McMurray, J. S. et al., *Peptide Res.*, 1994, 7, 195 and references cited therein.

The compounds of the invention have been found to be histone deacetylase inhibitors. As such, they may be useful in the treatment and prevention of protozoal diseases in human and animals, including poultry. Examples of protozoal diseases against which histone deacetylase inhibitors may be used, and their respective causative pathogens, include: 1) amoebiasis (Dientamoeba sp., *Entamoeba histolytica*); 2) giardiasis (*Giardia lamblia*); 3) malaria (Plasmodium species including *P. vivax, P. falciparum, P. malariae* and *P. ovale*); 4) leishmaniasis (Leishmania species including *L. donovani, L. tropica, L. mexicana*, and *L. braziliensis*); 5) trypanosomiasis and Chagas disease (Trypanosoma species including *T. brucei, T. theileri, T. rhodesiense, T. gambiense, T. evansi, T. equiperdum, T. equinum, T. congolense, T. vivax* and *T. cruzi*); 6) toxoplasmosis (*Toxoplasma gondii*); 7) neosporosis (*Neospora caninum*); 8) babesiosis (Babesia sp.); 9) cryptosporidiosis (Cryptosporidium sp.); 10) dysentary (*Balantidium coli*); 11) vaginitis (Trichomonas species including *T. vaginitis*, and *T. foetus*); 12) coccidiosis (Eimeria species including *E. tenella, E. necatrix, E. acervulina, E. maxima* and *E. brunetti, E. mitis, E. bovis, E. melagramatis*, and Isospora sp.); 13) enterohepatitis (*Histomonas gallinarum*), and 14) infections caused by Anaplasma sp., Besnoitia sp., Leucocytozoan sp., Microsporidia sp., Sarcocystis sp., Theileria sp., and *Pneumocystis carinii*.

Compounds of formula (I) are preferably used in the treatment or prevention of protozoal infections caused by a member of the sub-phyllum Apicomplexans. More preferably compounds of formula (I) are used in the treatment or prevention of malaria, toxoplasmosis, cryptosporidiosis and trypanosomiasis in humans and animals; and in the management of coccidiosis, particularly in poultry, either to treat coccidial infection or to prevent the occurrence of such infection.

Two specific examples of preventing the establishment of parasitic infections in humans and animals are 1) the prevention of Plasmodium (malaria) infection in humans in endemic areas and 2) the prevention of coccidiosis in poultry by administering the compound continuously in the feed or drinking water. Malaria is the number one cause of death in the world. The disease is transmitted by mosquitoes in endemic areas and can very rapidly progress to a life threatening infection. Therefore, individuals living in or visiting areas where malaria carrying mosquitoes are present routinely take prophylactic drugs to prevent infection. Compounds of formula (I) would be administered orally or parenterally one or more time(s) a day. The dose would range from 0.01 mg/kg to 100 mg/kg. The compound could be administered for the entire period during which the patient or animal is at risk of acquiring a parasitic infection.

Coccidiosis is a disease which can occur in humans and animals and is caused by several genera of coccidia. The most economically important occurrence of coccidiosis is the disease in poultry. Coccidiosis in poultry is caused by protozoan parasites of the genus Eimeria. The disease can spread quite rapidly throughout flocks of birds via contaminated feces. The parasites destroy gut tissue and therefore damage the gut lining impairing nutrient absorption. An outbreak of coccidiosis in a poultry house can cause such dramatic economic losses for poultry producers that it has become standard practice to use anticoccidial agents prophylactically in the feed. A compound of formula (I) would be administered in the feed or drinking water for a portion of, or for the entire life of the birds. The dose would range between 0.1 ppm to 500 ppm in the feed or water.

For treatment of established parasitic infections in humans or animals, compounds of formula (I) could be administered orally or parenterally once the infection is suspected or diagnosed. The treatment period would vary according to the specific parasitic disease and the severity of the infection. In general the treatment would be continued until the parasites were eradicated and/or the symptoms of the disease were resolved. Two specific examples are the treatment of a *Cryptosporidium parvum* infection in an animal or human and treatment of acute *Plasmodium falciparum* malaria in humans. *Cryptosporidium parvum* is a protozoan parasite that infects and destroys cells lining the intestinal tract of humans and animals. The infection establishes quite rapidly and has acute effects on the patient. In the case of humans, patients get severe dysentery for a period of 5–7 days. In immune compromised patients *C. parvum* infections can persist and can be life threatening. In animals *C. parvum* infection is the number one cause of death in young dairy calves. A *C. parvum* infection can be easily diagnosed by symptoms and examination of a stool sample. Once the disease is suspected and/or diagnosed treatment with a compound of formula (I) can be initiated. The dose would vary between 0.01 mg/kg to 500 mg/kg. Treatments would be one or more time(s) a day, orally or parenterally until the infection is eliminated. Routinely this dosing period would be 1–3 weeks.

*P. falciparum* causes acute life threatening malarial infections in humans. The infection if left untreated can quite often result in death of the patient. A malaria infection can be easily diagnosed by symptoms and examination of a blood sample from the patient. Treatment would be initiated following diagnosis. A compound of formula (I) would be administered one or more time(s) a day, orally or parenterally, until the infection was eliminated. The dose would range between 0.01 mg/kg to 200 mg/kg.

Compounds of formula (I) may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of protozoal diseases in human and animals, the dosage may range from 0.01 mg/kg to 500 mg/kg. For prophylactic use in human and animals, the dosage may range from 0.01 mg/kg to 100 mg/kg. For use as an anticoccidial agent, particularly in poultry, the compound is preferably administered in the animals' feed or drinking water. The dosage ranges from 0.1 ppm to 500 ppm.

The compositions of the present invention comprises a compound of formula (I) and an inert carrier. The compositons may be in the form of pharmaceutical compositions for human and veterinary usage, or in the form of feed composition for the control of coccidiosis in poultry.

The pharmaceutical compositions of the present invention comprise a compound of formula (I) as an active ingredient, and may also contain a pharmaceutically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, a compound of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, compounds of formula (I) may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a compound of formula (I) may be conveniently administered as a component of a feed composition. Suitable poultry feed composition will typically contain from about 1 ppm to about 1000 ppm, preferably from about 0.01% to about 0.1% percent, by weight of a compound of formula (I). The optimum levels will naturally vary with the species of Eimeria involved, and can be readily determined by one skilled in the art. Levels of a compound of formula (I) in poultry feed of from about 0.01% to about 0.1% percent by weight of the diet are especially useful in controlling the pathology associated with E. tenella, while the preferred concentration for similar control of intestinal-dwelling species is from about 0.01% to about 0.1% percent by weight of the diet. Amounts of about 0.01% to about 0.1% percent by weight are advantageous in reducing the pathogenic effects of both fecal and intestinal coccidiosis.

In the preparation of poultry feed, a compound of formula (I) may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal, calcium carbonate and vitamins.

Compositions containing a compound of formula I may also be prepared in powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The following examples are provided to more fully illustrated the present invention, and are not be construed as limiting the scope of the claims in any manner.

EXAMPLE 1

Antiprotozoal Activity

Compound of formula (I) may be evaluated against *Eimeria tenella, Toxoplasma gondii*, and *Plasmodium falciparum* according to methods reported in the literature.

(A) Activity against *E. tenella*

The visual assay using Madin Darby bovine kidney (MDBK) cell line as described in Schmatz, Crane and Murray, "*Eimeria tenella*: Parasite-Specific Incorporation of $^3$H-Uracil as a Quantitative Measure of Intracellular Development" *J. Protozoology*, 1986, 33(1):109–114 is generally followed to evaluate the compound's anti-Eimeria activity.

(B) Activity against *T. gondii*

The visual assay described in Roos et al, In: "Methods in Microbial Pathogenesis", *Methods in Cell Biology*, 1994, D. G. Russell, Ed., (Academic Press) is generally followed to evaluate the compound's anti-Toxoplasma activity.

(C) Activity against *P. falciparum*

The antimalarial activity is determined in a radioactive assay following the general protocol described in Desjardins et al, "Quantitative Assessment of Antimalarial Activity In Vitro by a Semiautomated Microdilution Technique" *Antimicrobial Agents and Chemotherapy* 1979, 16:710–718.

EXAMPLE 2

Competitive Binding Assay (HDA inhibition)

(a) Preparation of the lysates

Chick Liver. Livers from 3–5 three week old chickens are collected, rinsed in ice cold phosphate buffered saline (pH 7.4), diced into small pieces and rinsed again 3–4 times with ice cold 50 mM N-2-hydroxyethylpiperazine-N'-2-ethanesulfonic acid (HEPES) (pH 7.4) containing 0.1 mM phenylmethanesulfonyl fluoride (PMSF). The tissue is then resuspended in HEPES buffer, homogenized in a polytron homogenizer and centrifuged at 3000×g for 10 min. The supernatant is then subjected to an additional 100,000 g centifugation for 1 hour. The pellet and the floating layer of lipid are discarded and the supernatant, referred to as the chick liver S100 fraction, is retained for binding assays. After estimating the protein concentration, the supernatant (S100) is aliquoted and frozen at $-80°$ C.

*E. tenella* oocysts. Approximately $2 \times 10^9$ *E. tenella* oocysts are suspended in 5 ml of PBS/0.1 mM PMSF, 4 mls of an equal mixture (vol/vol) of 4.0 and 1.0 mm glass beads is added. The glass bead-oocyst mixture is then shaken for 20 minutes to cause disruption of the oocysts. The efficiency of breakage is checked microscopically. The resulting homogenate is separated from the glass beads and centrifuged at 3000×g for 10 min. The supernatant is then subjected to an additional centrifugation at 100,000 g for 1 hr. The is discarded and the supernatant, referred to as the *E. tenella* S100 fraction, is retained for binding assays. After estimating the protein concentration, the supernatant (S100) is aliquoted and frozen at $-80°$ C.

*P. berghei*. 22.5 mls of blood collected from mice infected with *P. berghei* malaria (with over 50% of the erythrocytes parasitized) is collected and treated with saponin (1:100 volume of 10% saponin in phosphate buffered saline (PBS)), held on ice for 15 min. to release the parasites and centrifuged at 2000×g for 10 min. The pellet is washed twice in PBS, and then frozen and thawed 3 times in a total vol of 2 ml PBS containing 0.1 mM PMSF (PBS/PMSF). PBS/PMSF is then added to bring the volume up to 10 ml and the suspension is centrifuged at 100,000×g for 1.5 hrs. The pellet is discarded and the supernatant, refered to as the *P. berghei* S100 fraction, is retained for binding assays. After estimating the protein concentration, the supernatant (S100) is aliquoted and frozen at −80° C.

(b) Assay

Each assay tube contains a final volume of 1 ml with 1.3 ng/ml of $^3$H-N-desmethoxyapicidin, 150–200 μg of the appropriate S100 supernatant and concentrations of potential HDA inhibitors from 0.001–10 μg/ml.

(i) labeled substrate. 2-$^3$H-N-desmethoxyapicidin (18.69 mCi/mg) is diluted 1:100 in ethanol, and 2 μl added per 1 ml of 50 mM HEPES pH 7.4 with 0.05% Triton-X100 (HEPES/Triton) is added. This provides 1.3 ng 2-$^3$H-N-desmethoxyapicidin /ml of assay (54,000 DPM/ml.)

(ii) potential HDA inhibitors. The stocks of the test compounds are made up to 2 mg/ml dimethylsulfoxide (DMSO). The stock solution is diluted to 1000, 100, 10, 1 and 0.1 μg/ml in ethanol where a full titration is required. Ethanol is used as a negative control, a 100 μg/ml solution of unlabeled N-desmethoxyapicidin is used as a positive control. Six μl of the test compound solution, the positive and negative controls are used for the assay.

(iii) supernatant from (a). The S100 sample is diluted to a

```
Xaa Ile Trp Xaa
1

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:4:

Pro Ile Trp Xaa
1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:5:

Pro Ile Trp Xaa
1

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:6:

Pro Ala Ala Xaa
1

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:7:

Pro Ala Ala Xaa
1

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:8:
```

```
Xaa Ala Ala Xaa
 1

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:9:

Xaa Ala Ala Xaa
 1

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:10:

Pro Phe Xaa Xaa
 1

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:11:

Pro Phe Xaa Xaa
 1

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:12:

Xaa Phe Xaa Xaa
 1

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:13:
```

Xaa Phe Xaa Xaa
1

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:14:

Xaa Leu Phe Xaa
1

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:15:

Xaa Leu Phe Xaa
1

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:16:

Pro Leu Phe Xaa
1

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:17:

Pro Leu Phe Xaa
1

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:18:

Pro Phe Phe Xaa
1

(2) INFORMATION FOR SEQ ID NO:19:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:19:

Pro Phe Phe Xaa
1

(2) INFORMATION FOR SEQ ID NO:20:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:20:

Xaa Leu Phe Xaa
1

(2) INFORMATION FOR SEQ ID NO:21:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:21:

Xaa Leu Phe Xaa
1

(2) INFORMATION FOR SEQ ID NO:22:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:22:

Xaa Ile Tyr Xaa
1

(2) INFORMATION FOR SEQ ID NO:23:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:23:

```
Xaa Ile Tyr Xaa
  1
```

(2) INFORMATION FOR SEQ ID NO:24:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:24:

```
Pro Ile Tyr Xaa
  1
```

(2) INFORMATION FOR SEQ ID NO:25:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:25:

```
Pro Ile Tyr Xaa
  1
```

(2) INFORMATION FOR SEQ ID NO:26:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:26:

```
Xaa Ile Tyr Xaa
  1
```

(2) INFORMATION FOR SEQ ID NO:27:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:27:

```
Xaa Ile Tyr Xaa
  1
```

(2) INFORMATION FOR SEQ ID NO:28:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:28:

```
Pro Ile Tyr Xaa
 1
```

(2) INFORMATION FOR SEQ ID NO:29:

(i) SEQUENCE CHARACTERISTICS:
       (A) LENGTH: 4 amino acids
       (B) TYPE: amino acid
       (C) STRANDEDNESS: single
       (D) TOPOLOGY: circular (ii) MOLECULE TYPE: peptide (xi) SEQUENCE DESCRIPTION: SEQ ID NO:29:

```
Pro Ile Tyr Xaa
```

What is claimed is:

1. A compound having the formula:

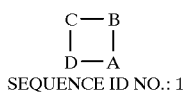

SEQUENCE ID NO.: 1 wherein

A is

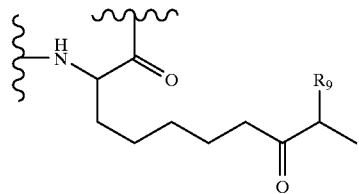

$R_9$ is H, OH, $OPO_3=$, $OC(O)R^a$, $OCO_2R^a$ or $OC(O)NR^aR^a$;

wherein $R^a$ is (1) optionally substituted $C_1$–$C_{10}$ alkyl, (2) optionally substituted $C_3$–$C_{10}$ alkenyl, (3) optionally substituted $C_3$–$C_{10}$ alkynyl, (4) optionally substituted aryl, (5) optionally substituted $C_3$–$C_8$ cycloalkyl (6) optionally substituted $C_5$–$C_8$ cycloalkenyl where the substitutents on the alkyl, alkenyl, alkynyl, aryl, cycloalkyl and cycloalkenyl are from 1 to 5 groups independently selected from hydroxy, $C_1$–$C_6$ alkoxy, $C_3$–$C_7$ cycloalkyl, aryl $C_1$–$C_3$ alkoxy and halogen, (7) $C_1$–$C_5$ perfluoroalkyl, (8) a 5- or 6-membered ring containing 1 to 4 heteroatoms selected from oxygen, sulfur and nitrogen optionally substituted by 1 to 4 groups independently selected from $C_1$–$C_5$ alkyl, $C_1$–$C_5$ alkenyl, $C_1$–$C_5$ perfluoroalkyl, amino or halogen, and which may be saturated or partly unsaturated;

B is selected from the group consisting of Alanine, Arginine, Asparagine, Aspartic Acid, Cysteine, Glutamine, Glutamic Acid, Glycine, Histidine, Isoleucine, Leucine, Lysine, Methionine, Ornithine, Phenylalanine, Proline, Serine, Threonine, Tryptophan, Tyrosine, Tyrosine(OMe), Valine, α-Aminobutyric Acid, β-Cyclohexyl-Alanine, Hydroxyproline, Pipecolic Acid, Norleucine, Norvaline and β-(2-Thienyl)-Alanine;

C is selected from the group consisting of Alanine, Arginine, Asparagine, Aspartic Acid, Cysteine, Glutamine, Glutamic Acid, Glycine, Histidine, Isoleucine, Leucine, Lysine, Methionine, Ornithine, Phenylalanine, Proline, Serine, Threonine, Tryptophan, Tyrosine, Tyrosine(OMe), Valine, α-Aminobutyric Acid, β-Cyclohexyl-Alanine, Hydroxyproline, Pipecolic Acid, Norleucine, Norvaline and β-(2-Thienyl)-Alanine;

D is selected from the group consisting of Proline, Pipecolic Acid, Glycine, Alanine, Hydroxyproline, α-Aminobutyric Acid, N-Methyl-Alanine and N-Methyl-Glycine; with the proviso that when B is tryptophan, C is not isoleucine or valine; or a pharmaceutically acceptable salt thereof.

2. The compound as defined in claim 1 which is selected from

[cyclo-(Pip-Ile-Trp-Aoh)]
[cyclo-(Pip-Ile-Trp-Aod)]
[cyclo-(Pro-Ile-Trp-Aoh)]
[cyclo-(Pro-Ile-Trp-Aod)]
[cyclo-(Pro-Ala-Ala-Aoh)]
[cyclo-(Pro-Ala-Ala-Aod)]
[cyclo-(Pip-Ala-Ala-Aoh)]
[cyclo-(Pip-Ala-Ala-Aod)]
[cyclo-(Pro-Phe-Aib-Aoh)]
[cyclo-(Pro-Phe-Aib-Aod)]
[cyclo-(Pip-Phe-Aib-Aoh)]
[cyclo-(Pip-Phe-Aib-Aod)]
[cyclo-(Pip-Leu-Phe-Aoh)]
[cyclo-(Pip-Leu-Phe-Aod)]
[cyclo-(Pro-Leu-Phe-Aoh)]
[cyclo-(Pro-Leu-Phe-Aod)]
[cyclo-(Pro-Phe-Phe-Aoh)]
[cyclo-(Pro-Phe-Phe-Aod)]
[cyclo-(Pip-Leu-Phe-Aoh)]
[cyclo-(Pip-Leu-Phe-Aod)]

[cyclo-(Pip-Ile-Tyr(OMe)-Aoh)]
[cyclo-(Pip-Ile-Tyr(OMe)-Aod)]
[cyclo-(Pro-Ile-Tyr(OMe)-Aoh)]
[cyclo-(Pro-Ile-Tyr(OMe)-Aod)]
[cyclo-(Pip-Ile-Tyr-Aoh)]
[cyclo-(Pip-Ile-Tyr-Aod)]
[cyclo-(Pro-Ile-Tyr-Aoh)]
[cyclo-(Pro-Ile-Tyr-Aod)]

where Aoh is 2-Amino-8-Oxo-9-Hydroxy-decanoic acid and Aod is 2-Amino-8-Oxo-Decanoic acid.

* * * * *